United States Patent
Hug et al.

(10) Patent No.: US 11,154,470 B1
(45) Date of Patent: Oct. 26, 2021

(54) ANTI-INFLAMMATORY AND SENOLYTIC DENTAL CARE PRODUCT WITH TOOTH WHITENING CHARACTERISTICS

(71) Applicant: Credentis AG, Windisch (CH)

(72) Inventors: Michael Hug, Zofingen (CH); Haleh Abivardi Brönner, Zürich (CH); Golnar Abivardi Signer, Cham (CH); Dominikus Amadeus Lysek, Windisch (CH)

(73) Assignee: vVardis AG, Baar (CH)

( * ) Notice: Subject to any disclaimer, the term of this patent is extended or adjusted under 35 U.S.C. 154(b) by 0 days.

(21) Appl. No.: 16/944,502

(22) Filed: Jul. 31, 2020

(51) Int. Cl.
   *A61K 8/24*   (2006.01)
   *A61K 8/64*   (2006.01)
   *A61Q 11/00*  (2006.01)
   *A61K 8/9789* (2017.01)

(52) U.S. Cl.
   CPC ............... *A61K 8/24* (2013.01); *A61K 8/64* (2013.01); *A61K 8/9789* (2017.08); *A61Q 11/00* (2013.01)

(58) Field of Classification Search
   CPC .................................................... A61K 31/70
   USPC ........................................................ 435/375
   See application file for complete search history.

(56) References Cited

PUBLICATIONS

China, 104306844_DERWEN, Jan. 2015, China, Chen S.*
Delfino et al., Effectiveness of Home Bleaching Agents in Discolored Teeth and Influence on Enamel Microhardness, J Appl Oral Sci. 2009;17(4):284-8.
Dahl, Tooth Bleaching—a Critical Review of the Biological Aspects, Crit Rev Oral Biol Med, 14 (4):292-304, 2003.
Dabanoglu et al., Whitening effect and morphological evaluation of hydroxyapatite materials, American Journal of Dentistry, vol. 22, No. 1, p. 23-29, 2009.
Demarco et al., Over-the-counter whitening agents: a concise review, Braz Oral Res, 23(Spec Iss 1):64-70, 2009.
Gerlach et al., Objective and subjective whitening response of two self-directed bleaching system, American Journal of Dentistry, vol. 15, Special Issue, p. 7A-12A, 2002.
Jiang et al., Beneficial effects of hydroxyapatite on enamel subjected to 30% hydrogen peroxide, Journal of Dentistry, 26, p. 907-914, 2008.
Jin et al., Efficacy of tooth whitening with different calcium phosphate-based formulations, Eur J Oral Sci, 121: 382-388, 2013.
Lim et al., Hydroxyapatite coating on damaged tooth surfaces by immersion, Biomed. Mater. 4, 025017 (7pp), 2009.
Janurudin et al., Preparation of a hydroxyapatite and hydrogen peroxide composite for tooth whitening, Bio-Medical Materials and Engineering 17, 69-75, 2007.
Nagelberg, Tooth whitening, https://www.dentaleconomics.com/practice/article/16390423/tooth-whitening, 2014.
Niwa et al., Polishing and whitening properties of toothpaste containing hydroxyapatite, Journal of Materials Science: Materials in Medicine 12, 277-281, 2001.
Raoufi et al., Effect of whitening toothpastes on tooth staining using two different colour-measuring devices—a 12-week clinical trial, International Dental Journal, 60, p. 419-423, 2010.
Rezk et al., Assessment of cytotoxicity exerted by leaf extracts from plants of the genus *Rhododendron* towards epidermal keratinocytes and intestine epithelial cells, BMC Complementary and Alternative Medicine, 15:364, 2015.
Rodrigues et al., Enamel Remineralization by Fluoride-Releasing Materials: Proposal of a pH-Cycling Model, Braz Dent J, 21(5): 446-451, 2010.
Roveri et al., Surface Enamel Remineralization: Biomimetic Apatite Nanocrystals and Fluoride Ions Different Effects, Journal of Nanomaterials vol. 2009, Article ID 746383, 9 pages.

\* cited by examiner

*Primary Examiner* — Walter E Webb
(74) *Attorney, Agent, or Firm* — Thomas | Horstemeyer LLP

(57) ABSTRACT

The present invention relates to the field of dental care, e.g., with toothpaste, tooth gel, mouth-wash, mouth spray or oral care foam. In particular, it provides an anti-inflammatory and senolytic dental care product with tooth whitening characteristics. The dental care product comprises calcium phosphate particles of a specific size, the self-assembling peptide P11-4 or oligopeptide 104 of SEQ ID NO: 1, an extract of a plant of the genus *Rhododendron*, preferably, an alpine rose or Alpenrose such as *Rhododendron ferrugineum* or *Rhododendron hirsutum*, and an extract of a plant of the genus *Leontopodium*, such as *Leontopodium nivale*, which is also called Edelweiss. The dental care product may further comprise an extract of a plant of the genus *Eleutherococcus*, such as *Eleutherococcus senticosus*, which is also designated Siberian ginseng or *Acanthopanax senticosus*. In addition to the proven tooth whitening characteristics of said product, which can be a medicinal product or a pharmaceutical composition, it further has a senolytic and anti-inflammatory effect. Thus, the invention provides a method for tooth whitening as well as a method of treating periodontal disease, and/or for eliminating or reducing the number of senescent cells in the gums of a subject. The gums of a subject can thus be rejuvenated, potential loose teeth stabilized, and the well-being increased.

23 Claims, No Drawings
Specification includes a Sequence Listing.

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: P11-4 / oligopeptide 104

<400> SEQUENCE: 1

Gln Gln Arg Phe Glu Trp Glu Phe Glu Gln Gln
1               5                   10
```

ANTI-INFLAMMATORY AND SENOLYTIC DENTAL CARE PRODUCT WITH TOOTH WHITENING CHARACTERISTICS

The present invention relates to the field of dental care, e.g., with toothpaste, tooth gel, mouthwash, mouth spray or oral care foam. In particular, it provides an anti-inflammatory and senolytic dental care product with tooth whitening characteristics. The dental care product comprises calcium phosphate particles of a specific size, the self-assembling peptide P11-4 or oligopeptide 104 of SEQ ID NO: 1, an extract of a plant of the genus *Rhododendron*, preferably, an alpine rose or Alpenrose such as *Rhododendron ferrugineum* or *Rhododendron hirsutum*, and an extract of a plant of the genus *Leontopodium*, such as *Leontopodium nivale*, which is also called Edelweiss. The dental care product may further comprise an extract of a plant of the genus *Eleutherococcus*, such as *Eleutherococcus senticosus*, which is also designated Siberian ginseng or *Acanthopanax senticosus*. In addition to the proven tooth whitening characteristics of said product, which can be a medicinal product or a pharmaceutical composition, it further has a senolytic and anti-inflammatory effect. Thus, the invention provides a method for tooth whitening as well as a method of treating periodontal disease, and/or for eliminating or reducing the number of senescent cells in the gums of a subject. The gums of a subject can thus be rejuvenated, potential loose teeth stabilized, and the well-being increased.

Periodontal disease, also known as gum disease, is a set of inflammatory conditions affecting the periodontium, i.e., the tissues that surround and support the teeth. In its early stage, called gingivitis, the gums become swollen, red, and may bleed. In its more serious form, called periodontitis, the gums can pull away from the tooth, bone can be lost, and the teeth may loosen or fall out. Bad breath may also occur.

Periodontal disease is caused by microorganisms that adhere to and grow on the tooth's surfaces, along with an over-aggressive immune response against these microorganisms. With the destruction of the gingival fibers, the gum tissues separate from the tooth, leading to deepened sulcus, called a periodontal pocket. Subgingival micro-organisms, i.e., those that exist apically from gum line, colonize the periodontal pockets and cause further inflammation in the gum tissues and progressive bone loss. If left undisturbed, microbial plaque calcifies to form calculus, which is commonly called tartar. Tissue destruction, e.g., of periodontal ligament, and alveolar bone resorption can ultimately lead to tooth mobility and subsequent loss of involved teeth.

In the early stages, periodontitis has very few symptoms, and in many individuals the disease has progressed significantly before they seek treatment. A diagnosis of periodontitis is established by inspecting the soft gum tissues around the teeth with a probe (i.e., a clinical examination) and by evaluating the patient's X-ray films (i.e., a radiographic examination), to determine the amount of bone loss around the teeth.

Treatment involves good oral hygiene and regular professional teeth cleaning. Recommended oral hygiene include daily brushing and flossing. In certain cases antibiotics or dental surgery may be recommended. Globally 538 million people were estimated to be affected in 2015. In the United States nearly half of those over the age of 30 are affected to some degree, and about 70% of those over 65 have the condition. Factors that increase the risk of disease include smoking, diabetes, HIV/AIDS, family history, and certain medications (https://en.wikipedia.org/wiki/Periodontal_disease).

A few years ago, Dr. Charles Cobb analysed insurance submissions for all dental services. Approximately 50% of adults between the ages of 30 and 70 have some degree of periodontitis; however, his evaluation revealed that periodontal therapy of all kinds accounts for only 5% to 6% of the total benefit codes submitted to insurance carriers. At the same time, insurance submissions for a variety of cosmetic services, such as in tooth whitening, have risen significantly (Nagelberg, R. H., 2014. https://www.dentaleconomics.com/practice/article/16390423/tooth-whitening).

Both extrinsic and intrinsic reasons contribute to discoloration of teeth. For example, coffee, tea, wine, carrots, oranges or tobacco can leave stains on the enamel surface. Certain antibiotics, excessive fluoride uptake or hereditary diseases can cause intrinsic discoloration. Tooth discoloration can be an important aesthetic problem for dental patients. For example, in the UK, around 20% of people are dissatisfied with their teeth colour. In the USA, 34% seem to be dissatisfied.

Often, superficial stains can be removed by thorough cleaning of teeth by the patient or a health professional. Polishing with abrasive material is sometimes used to this end, for example employing pastes which comprise particles of calcium phosphate, chalk, pumice or silica. If the patient desires a further more intrinsic reduction in teeth discoloration, chemical bleaching is the classical option. Various bleaching techniques are known, which are based upon an oxidizing agent such as peroxide. Bleaching can be performed by a health professional in a dental clinic or by the patient at home. For this, prescription products for overnight bleaching or bleaching toothpastes can be used.

However, in recent years, awareness of side effects associated with bleaching, such as demineralisation, erosion and tooth sensitivity caused by peroxides, has increased (e.g., Dahl et al., 2003) and concentrations of higher than 0.1% peroxide were even banned in the European Union since 2012 for publicly available cosmetic products. It has been suggested to use hydroxyapatite nanocrystals to remineralize tooth surfaces damaged e.g., by bleaching (Mohd et al., 2007, Jiang et al., 2008, Lim et al., 2009, Roveri et al., 2009). Hydroxyapatite crystalline particles, which closely mimic the natural material of the tooth, can be deposited on the tooth enamel. In addition to filling in scratches or eroded parts of a tooth, and prevention or treatment of caries, deposited hydroxyapatite can counteract hypersensitivity of teeth caused by exposition of dentin tubule upon recession of gums (WO 2007/137606 A1).

Amorphous Calcium Phosphate stabilised with phosphoproteins such as caseinphosphopeptide (CPP-ACP) has been used in oral care products for preventing and treating caries lesions (z.B. US 20050037948 A1, US 20080075675 A1, US 20100297203 A1).

It was found that calcium phosphate such as hydroxyapatite in particulate form also has whitening properties independent of bleaching or polishing (Niwa et al., 2001, Dabanoglu et al, 2009). Dabanoglu et al. compared different materials, e.g., nano-hydroxyapatite or nano-tricalcium phosphate or a dissolvable polymer film (methacrylic acid-ethyl acrylate copolymers) comprising nano-hydroxyapatite with regard to their whitening properties. They achieved a colour change, measured spectrometrically as $\Delta E$ (L*a*b scale), with all tested materials. Measurement can be performed according to ISO 28399. The effect increased with three applications to a $\Delta E$ of about 3, which decreased with some materials after subjecting the treated teeth to shear force. It is noted that the average casual viewer can notice the difference between two colours that are 3-4 $\Delta E$ apart. A trained eye can differentiate between two colours that are 2-3 ΔE apart. Thus, while a perceivable change could be generated, there is still room for improvement.

WO 2013/068020, JPH115722, JP2008/081424, JP 2007/0176862, JP 2001/131041, CN101385856 disclose a dental care product comprising hydroxyapatite in combination with different agents such as lactoferrin, hydrolyzed silk or lysozyme.

Raoufi et al., 2010, have compared a commercial over the counter calcium peroxide toothpaste and a hydroxyapatite toothpaste (intended for bleaching or whitening teeth, respectively) with a fluoride placebo toothpaste, and found no objective whitening effect for any of the toothpastes in a 12 week clinical trial.

WO 2015/044268 A1 provides a much more potent dental care product capable of tooth whitening, comprising 0.4-60 wt % mineral particles such as hydroxyapatite, the particles having a size of 10 nm-50 μm, and 0.001-5 wt %, preferably, 0.02-2 wt %, 0.04-1 wt %, 0.05-0.5 wt %, 0.05-0.2 wt % of an organic compound capable of forming a hydrogel, preferably, a self-assembling peptide such as P 11-4, which is also designated oligopeptide 104 (SEQ ID NO: 1). It teaches that, by mixing mineral particles with a suitable organic matrix such as a suitable protein matrix in a dental care product according to the invention, the previously described whitening effect of hydroxyapatite particles on teeth can be significantly increased. The protein alone also does not achieve comparable effects, and the combination works in a synergistic manner. In particular, the invention provides a dental care product capable of producing a difference in whiteness of a tooth, measured on CIELAB (=L*a*b*) scale, of ΔE of more than 5 after 3 applications, preferably, ΔE of more than 5 after 1 application.

Self-assembling peptide have also been taught to be effective in treatment of gingivitis, periodontitis and peri-implantitis (WO 2018/033570 A1). However, the described treatment requires cleaning and/or debridement of at least one tooth affected by the disease, and insertion of the composition into a pocket adjacent to said tooth caused by gum and/or bone recession caused by the oral disease.

In light of this, the inventors addressed the problem of providing a dental care material that is both suitable for tooth whitening and, at the same time, for treating, preventing or reducing incidence of gingivitis, periodontitis and peri-implantitis. The problem is solved by the invention, in particular, by the subject-matter of the claims.

The invention provides a dental care product comprising a) 0.4-40 wt % calcium phosphate particles having a size of 0.01-50 μm, b) 0.001-5 wt % of a self-assembling peptide consisting of SEQ ID NO: 1, c) 0.1-5 wt % of an extract of a plant of the genus *Rhododendron*, and d) 0.1-5 wt % of an extract of a plant of the genus *Leontopodium*.

As previously stated, tooth whitening products comprising calcium phosphate and self-assembling peptides are already known in the art, e.g., from WO 2015/044268 A1, which is herewith fully incorporated herein. The compositions and features described in WO 2015/044268 A1 can be used in the context of the present invention when combined with the extracts described herein.

Self-assembling peptides are capable of forming a protein matrix or hydrogel through self-assembly. Preferably, the protein matrix is present in the dental care product in the form of a hydrogel, i.e. the proteins (e.g., self-assembling peptides), are not present as monomers.

The inventors have shown that a matrix of said self-assembling peptide and the calcium phosphate particles on the tooth surface can be formed, which has an increased whitening effect compared to the layer of mineral particles deposited on the tooth surface with previous methods (e.g., Dabanoglu et al, 2009). The structures incorporating the mineral particles of the present invention are believed to be pre-formed in the dental care product and stable under oral conditions. They are also at least partly resistant to brushing with an ultrasound toothbrush.

Self-assembling peptides have been provided, e.g., in WO 2004/007532 A1, which is fully incorporated herein by reference. WO 2004/007532 A1 discloses peptides that are capable of forming three-dimensional scaffolds, thereby promoting nucleation of de-novo calcium phosphate. These artificial peptides assemble in one dimension to form beta-sheet, and higher order assemblies such as tape-like assemblies. Three-dimensional supramolecular structures of self-assembling proteins can be formed, which have an affinity for/to calcium phosphate.

Several other self-assembling peptides (SAP) which may be employed have been described in the prior art. For example, WO 2010/041636 A1 describes a bioadsorbable peptide tissue occluding agent containing an artificial peptide having 8-200 amino acid residues with the hydrophilic amino acids and hydrophobic amino acids alternately bonded, which self-assembles into a beta-structure at physiological pH. Self-assembling peptides with alternating hydrophobic and hydrophilic residues or stretches which interact with the extracellular matrix are also disclosed in WO 2008/113030 A2. WO 2010/103887 A1 discloses self-assembling peptides, which comprise basic, hydrophobic and acidic amino acids of a specific primary sequence and peptide gels thereof which have high strength. WO2010/019651 A1 relates to other self-assembling peptides.

Another application, WO 2007/000979 A1, describes self-assembling peptides with polar and non-polar amino acids. The peptides are capable of forming a beta-sheet structure in which the non-polar amino acid residues are arranged on one side of the structure in the assembled form. Amphiphilic self-assembling peptides for use as stable macroscopic membranes, which are used in biomaterial applications, such as slow-diffusion drug delivery, are described in U.S. Pat. No. 6,548,630.

EP 2 327 428 A2 refers to a pharmaceutical composition comprising self-assembling peptide nanofibers, which are complementary to each other, and at least one cell for repairing damaged tissue, such as tissue after a myocardial infarction.

In the context of the present invention, the self-assembling peptides taught in WO 2004/007532 A1 are specifically advantageous, in particular, the self-assembling peptide designated oligopeptide 104 (SEQ ID NO: 1, QQRFEWEFEQQ.)

Self-assembling peptides may be modified peptides comprising an Ac-N-terminus and/or NH2-C-terminus, or non-modified peptides. Preferably, they have an Ac-N-terminus and/or NH2-C-terminus.

Preferably, the concentration of self-assembling peptide is 0.001-0.5 wt %, optionally, 0.01-0.05 wt %.

The self-assembling peptide is able to bind the calcium phosphate particles and adhere to the tooth surface. The matrix thus comprises binding sites for the calcium phosphate particles which enable it to bind the particles on the tooth surface. For example, charged amino acid residues such as Glu on the surface of self-assembling peptides bind to hydroxyapatite particles and to the tooth surface, which is also substantially formed of hydroxyapatite. Without intending to be bound by the theory, it is believed that both reactions increase the stability of the formed complex to generate a more permanent whitening effect. A capability for three-dimensional self-organization, which is found in the self-assembling peptides is important for binding. In general, highly charged surfaces will promote adhesion of the calcium phosphate particles. The protein-matrices work particularly well when their surface shows glutamate residues which may attach to calcium phosphate or to other mineral particles, as in SEQ ID NO: 1.

The dental care product further comprises a fluorophore. Trp is a preferred fluorophore. Said fluorophore is an amino acid residue of the self-assembling peptide matrix, preferably Trp, Tyr and/or Phe. The self-assembling peptide of SEQ ID NO: 1 comprises such fluorophores.

Optionally, the dental care product comprises a further fluorophore that is no amino acid residue of the self-assembling peptide, and which in one embodiment is not covalently bound to the self-assembling peptide. Covalent linkage of a fluorophore to the self-assembling peptide is also envisioned. For example, the fluorophore may be a derivative of phthalocyanine, e.g., copper phthalocyanine (covarin blue). Embedding such a fluorophore into the combination of matrix and mineral particles as described above surprisingly leads to a more permanent and more intense whitening effect compared to incorporation of such fluorophores into a conventional toothpaste. However, addition of a further fluorophore to a dental care product of the invention is not required to achieve the whitening effect, as the self-assembling peptide comprises a fluorescent amino acid residue as described above.

A calcium phosphate particle, as used herein, comprises calcium phosphate. Calcium phosphate may, in the context of the present invention, be monocalciumphosphat-monohydrate (MCPM) $Ca(H_2PO_4)_2 \cdot H_2O$, monocalciumphosphate anhydrate (MCPA) $Ca(H_2PO_4)_2$, dicalciumphosphate dihydrate (DCPD, Brushit), $CaHPO_4 \cdot 2H_2O$, dicalciumphosphate anhydrate (DCPA, Monetit) $CaHPO_4$], Octacalciumphosphate (OCP) $Ca_8(HPO_4)_2(PO_4)_4 \cdot 5H_2O$, α-tricalciumphosphate (α-TCP) α-$Ca_3(PO_4)_2$, β-tricalciumphosphate (β-TCP) β-$Ca_3(PO_4)_2$, amorphous calcium phosphate (ACP) $Ca_x(PO_4)_y \cdot nH_2O$, calcium-deficient hydroxyapatite (CDHA) $Ca_{10}$-x$(HPO_4)_x(PO_4)_6$-x$(OH)_{2-x}$ (0<x<1), hydroxyapatite (HA) $Ca_{10}(PO_4)_6(OH)_2$, or tetracalciumphosphate (TTCP) $Ca_4(PO_4)_2O$, or a mixture of different calcium phosphates. In a preferred embodiment, it may also be particle comprising a calcium phosphate, e.g., a hydroxyapatite shell and a calcium carbonate core (e.g., Omyadent® 100 available from Omya, Oftringen, Switzerland).

In one embodiment, the particles or have a degree of crystallinity of 40% or more, e.g., 40-60%, 60% or more, 80% or more or 90% or more, or they are crystals. A higher degree of crystallinity is expected to make the effect on whiteness of teeth more long-lasting. Throughout the invention, the calcium phosphate preferably is hydroxyapatite. The hydroxyapatite may be substituted hydroxyapatite e.g., carbonate hydroxyapatite and zinc carbonate hydroxyapatite, or pure calcium phosphate, preferably, in crystalline form. In the context of the invention, reference to calcium phosphate or hydroxyapatite includes reference to derivatised calcium phosphates or hydroxyapatites of this kind unless otherwise mentioned. Of course, the calcium phosphate or hydroxyapatite particle may also consist of $CaPO_4$ (and of course crystal water as appropriate for the respective crystal form) only.

The hydroxyapatite particles may be obtained according to methods disclosed, e.g., in Roveri, Battistelli et al., 2009, EP 1 762 215 A1, US 20050037948 A1, US 20080075675 A1, US 20100247589 A1, US 20100297203 A1, WO 2007/137606 A1, or WO 2013/068020 A1. Preferably, the hydroxyapatite is obtainable according to WO 2007/137606 A1 and can be commercially obtained from Budenheim, Budenheim, Germany.

The size of the calcium phosphate particles preferably is measured by granulometry, e.g., with a light scattering particle size distribution analyzer (such as LA-950, Horiba, Kyoto, Japan). The form of the crystals preferably is needle-shaped, but it may also be rod-shaped or acicular.

The size of the particles is 10 nm-50 μm, preferably, 0.1 μm-25 μm. In one embodiment, the size is 10-1200 nm. The preferred size is 200-600 nm. In the context of the invention, this means that at least 30%, at least 50% or at least 80%, preferably, at least 90% of particles, e.g., at least 95% or 100% of the particles have the respective size.

In one embodiment, 30-100% or 50-90% of particles have a size of 200-600 nm. This size was selected for the experiments as it is corresponds to the wavelength of UV light or visible light, which plays an important role in white appearance of teeth. In the context of the invention, "about" means+1-10%, preferably, +1-5%.

In one embodiment, the particles have a mixture of different sizes, which may provide a still more intense whitening effect. In particular, for example 30-70% of particles may have a size of 200-400 nm, 30-70% of particles have a size of 400-600 nm, and, optionally, 30-70% of particles have a size of 10-200 nm. Alternatively, for example, 30-70% of particles may have a size of about 10-15 μm, about 30-70% of particles have a size of about 4-10 μm and, optionally, about 10-40% of particles have a size of 0.1-4 μm (all referring to wt %).

In a preferred embodiment, the particles are hydroxyapatite particles having a size of 1-25 μm, e.g., 4-20 μm.

In contrast to the tooth whitening products described in the prior art, the dental care product of the present invention further comprises at least two or at least three specific plant extracts.

In particular, the dental care product of the invention comprises an extract of a plant of the genus *Rhododendron*, preferably, of the subgenus *Rhododendron* L, as classified by Chamberlain 1996. This subgenus is characterized by small leafs or lepidotes, i.e., scales on the underside of the leaves. Plants from the section *Pognathum* from the Himalaya and adjacent mountains and the section *Rhododendron* L. from the temperate to subarctic Northern Hemisphere are typically used, in particular, plants from the Alps. Advantageously, the extract is from *Rhododendron ferrugineum* or *Rhododendron hirsutum*. *Rhododendron ferrugineum* extracts have been used in the experiments underlying the invention, but it is expected that extracts from closely relates species can also be used, especially, from other alpine roses.

*Rhododendron ferrugineum* (sometimes called alpine rose or alpenrose, snow-rose, or rusty-leaved alpenrose) is an evergreen shrub that grows just above the tree line in the Alps, Pyrenees, Jura and northern Apennines, on acid soils. It is the type species for the genus *Rhododendron*. It may grow up to 1 m tall and produces clusters of pinkish-red, bell-shaped flowers throughout the summer. The undersides of the leaves are covered in rust-brown spots. This is in contrast to *Rhododendron hirsutum*, which has no such brown colouring, has hairy edges to the leaves and grows over limestone. Where the two species co-occur (usually on soils of intermediate pH), the hybrid *Rhododendron×inter-* medium may occur; as its name suggests, it is intermediate in form between the two parental species, and which can also be used in the context of the invention. The alpine rose is one of the most typical and prominent Alpine, e.g., Swiss alpine plants. It grows at high altitudes and has developed impressive strategies to protect itself against dehydration and the attack of radicals and pathogens.

The extract may be an extract of the leaves and/or flowers of the plant, optionally, of the leaves and flowers of the plant. For example, the leaves and/or flowers can be harvested, which is sustainable, because they are regenerated the following year. Preferably, it is a leaf extract.

It has been shown that an extract has advantageous characteristics, it particular, it is capable of
- inhibiting UVA-induced photo-aging (protein carbonylation)
- exhibiting a senolytic effect, i.e., it eliminates senescent cells while not affecting healthy cells in a negative way. This rejuvenates the entire tissue as senescent cells contribute to inflammation and aging.
- significantly reducing redness and increase elasticity.

The extract further has potent anti-microbial effects, e.g., against bacteria involved in periodontal disease.

This applies for an alcoholic, e.g., ethanolic extract, methanolic extract, an oil, e.g., sunflower oil extract, propylene glycolic extract, a PEG extract, a hexane extract, a $CO_2$ extract or a glycerinic extract or dry extract. In the context of the dental care product of the invention, it may be desired to provide a product that does not comprise ethanol, methanol, hexane, PEG or propylene glycol. Thus, a glycerinic extract or dry extract may be advantageously used, e.g., a glycerinic extract. The glycerinic extract may further comprise water. Extracts of *Rhododendron ferrugineum* are, e.g., available from Mibelle Biochemistry, Mibelle AG (Buchs, Aargau, Switzerland).

The dental care product may comprise, e.g., 0.1-5 wt %, e.g., 0.5-3 wt % of said extract. Use at 1-2 wt % has been found to be advantageous. The extract may e.g., be a leaf extract extracted at a drug to extract ratio of 1:10 to 1:100, preferably, about 1:50, e.g., with glycerine.

The inventors have found that it is particularly advantageous to combine the dental care product of the invention comprising an extract from a plant of the genus *Rhododendron* with an extract of a plant of the genus *Leontopodium*. Probably due to its high content of anti-oxidants, said extract has anti-inflammatory properties and advantageously synergizes with the *Rhododendron* extract in treating the gums of a subject as further explained below, e.g., in treatment of gingivitis, periodontitis and peri-implantitis, as well as in rejuvenating the gums.

Thus, the dental care product further comprises 0.1-5 wt % of an extract of a plant of the genus *Leontopodium*. The dental care product may e.g. comprise 0.5-3 wt % of said extract. Use at 1-2 wt % has been found to be advantageous.

Said plant of the genus *Leontodium* may be *Leontopodium nivale, Leontopodium albogriseum, Leontopodium andersonii, Leontopodium antennarioides, Leontopodium artemisiifolium, Leontopodium aurantiacum, Leontopodium beerianum, Leontopodium blagoveshczenskyi, Leontopodium brachyactis, Leontopodium calocephalum, Leontopodium campestre, Leontopodium chuii, Leontopodium conglobatum, Leontopodium coreanum, Leontopodium dedekensii, Leontopodium delavayanum, Leontopodium discolor, Leontopodium fangingense, Leontopodium fauriei, Leontopodium forrestianum, Leontopodium franchetii, Leontopodium giraldii, Leontopodium gracile, Leontopodium haastioides, Leontopodium haplophylloides, Leontopodium hayachinense, Leontopodium himalayanum, Leontopodium jacotianum, Leontopodium japonicum, Leontopodium kamtschaticum, Leontopodium kurilense, Leontopodium leiolepis, Leontopodium leontopodinum, Leontopodium longifolium, Leontopodium melanolepis, Leontopodium meredithae, Leontopodium micranthum, Leontopodium microphyllum, Leontopodium monocephalum, Leontopodium muscoides, Leontopodium nanum, Leontopodium niveum, Leontopodium ochroleucum, Leontopodium omeiense, Leontopodium palibinianum, Leontopodium pusillum, Leontopodium roseum, Leontopodium rosmarinoides, Leontopodium shinanense, Leontopodium sinense, Leontopodium smithianum, Leontopodium souliei, Leontopodium stellatum, Leontopodium stoechas, Leontopodium stoloniferum, Leontopodium stracheyi, Leontopodium subulatum, Leontopodium villosulum, Leontopodium villosum, Leontopodium wilsonii*. Preferably, it is an alpine *Leontododium*, such as *Leontopodium nivale*, which is also designated Edelweiß.

The extract may be an extract of the leaves and/or flowers of the plant, preferably, of the leaves and flowers of the plant. The extract may e.g., be a leaf and flower extract extracted at a drug to extract ratio of 1:10 to 1:100, preferably, about 1:50, e.g., with glycerine. It has anti-oxidant and anti-inflammatory characteristics. Adsorption and elimination of free radicals is improved, which helps to combat aging of the gums. The high content of tannins also has a protective effect. The tannins also improve elasticity and contribute to regeneration of the gums. Flavoinoids protect the vasculature. Phenylpropanoids have adstringend effects. The blood circulation is stimulated, cell activity improved, and thus, in particular, in combination with the active agents from the *Rhododendron* extract, the regeneration of the tissue is stimulated.

This applies for an alcoholic, e.g., ethanolic extract, methanolic extract, an oil, e.g., sunflower oil, extract, a propylene glycolic extract, a PEG extract, a hexane extract, a $CO_2$ extract or a glycerinic extract or dry extract. In the context of the dental care product of the invention, it may be desired to provide a product that does not comprise ethanol, methanol, hexane, PEG or propylene glycol. Thus, a glycerinic extract or dry extract may be advantageously used, e.g., a glycerinic extract. The glycerinic extract may further comprise water. *Leontopodium Alpinum* Flower/Leaf Extract is, e.g., available from Lipoid Kosmetik AG (Steinhausen, Switzerland).

Optionally, the dental care product of the invention further comprises e) an extract of a plant of the genus *Eleutherococcus*, optionally, *Eleutherococcus senticosus*. *Eleutherococcus senticosus* is a species of small, woody shrub in the family Araliaceae native to Northeastern Asia. It may be colloquially called Siberian ginseng, devil's bush, eleuthero, ciwujia, Devil's shrub, shigoka, touch-me-not, wild pepper, or kan fang. Another synonym is *Acanthopanax senticosus*. *E. senticosus* has a history of use in folklore and traditional Chinese medicine. Typically, root extracts of *E. senticosus* are sold as a dietary supplement or cosmetic, usually under the name Siberian ginseng.

In the context of the present invention, the extract may be an extract of the roots, berries and/or leaves of the plant, optionally, of the whole of the plant. Preferably, it is an extract of the roots.

It has been demonstrated that polyphenolic compounds are the dominant majority of biologically active substances in the root, and, in the extract that may be used in the inventive product. These components confer beneficial properties to the Siberian Ginseng, such as anti-inflammatory, anti-irritant and anti-stress activities. In a screening of botanicals, these were selected based on their anti-inflammatory activity in blood samples, and a root extract of *Eleutherococcus senticosus* was found to be one of the nine most active anti-inflammatory extracts. Such extracts can thus advantageously be used in the context of the invention, and further contribute to the anti-inflammatory and anti-aging effect. The extract also improves wound healing.

Because the active anti-inflammatory agents can be found in an alcoholic, e.g., ethanolic extract, methanolic extract, an oil, e.g., sunflower oil extract, propylene glycolic extract, a PEG extract, a hexane extract, a $CO_2$ extract or a glycerinic extract or dry extract, the results of the anti-inflammatory study can be considered as valid for all these extracts. In the context of the dental care product of the invention, it may be desired to provide a product that does not comprise ethanol, methanol, hexane, PEG or propylene glycol. Thus, a glycerinic extract or dry extract may be advantageously used, e.g., a glycerinic extract. Extracts are available, e.g., as Herbasol® Pro extracts, from Lipoid Kosmetik AG (Steinhausen, Switzerland). In the context of the dental care product of the invention, it may be desired to provide a product that does not comprise ethanol or propylene glycol. Thus, e.g., a glycerinic extract may be advantageously used. The glycerinic extract may further comprise water.

The dental care product of the invention may comprise, e.g., 0.1-5 wt % of said extract of a plant of the genus *Eleutherococcus*, e.g., 0.5-2 wt % of said extract. Typically, 1-2 wt % are comprised, if said extract is present. The extract may e.g., be a root extract extracted at a drug to extract ratio of 1:10 to 1:100, preferably, about 1:50, e.g., with glycerine.

Optionally, the dental care product of the invention, comprising the herb extract of c), and, optionally of d) and/or e), may further comprise additional herb extracts, e.g., from peppermint, chamomile, and/or Chinese herbs e.g., *Centella Asiatica, Magnolia officinalis, Panax ginseng* or *Bletilla Striata*.

Preferably, the dental care product does not contain ethanol. Thus, in a preferred embodiment, all herb extracts contained are non-alcoholic extracts, e.g., glycerinic, oil extracts or dry extracts. Such glycerinic extracts may also comprise other ingredients or solvents, preferably water, but they do not comprise ethanol. The dental care product of the invention may be halal and/or vegan.

The dental care product is selected from the group comprising toothpaste, tooth gel, tooth mousse mouthwash, mouth spray and oral care foam.

The toothpaste can be a toothpaste for a conventional toothbrush, but it can also be a toothpaste for an ultrasonic toothbrush. In one embodiment, the dental care product is not a liquid, but a paste or gel, most preferably, it is a toothpaste or a tooth gel comprising 0.5-40 wt % of said calcium phosphate particles and 0.002-1 wt %. preferably, 0.05-0.5 wt % of said self-assembling peptide. A gel is a nonfluid colloidal network or polymer network that is expanded throughout its whole volume by a fluid. In the case of a hydrogel, the fluid is water. In contrast to a liquid, a gel has a finite, usually rather small, yield stress. The toothpaste may contain fluoride as sodium fluoride or sodium monofluorphosphate with a fluoride content of up to 1500 ppm.

The dental care product may additionally comprise one or more typical ingredients of the respective dental care product. Such typical ingredients may be:

abrasive agents such as carbonates, phosphates, silicates, acrylates, alumina,
suspension agents such as glycerine, polyethylene glycols (PEG), sorbitol, xylitol,
binding agents such as cellulose and derivate thereof, carrageenan, paraffin, xylose,
detergents such as hydrogenated castor oil, sodium lauryl sulphate, cocamidopropyl betaine
aroma such as caramel, vanillin, menthol, synthetic aroma
conserving agent such as, sodium benzoate, potassium sorbate, propylene glycol, parabens,
colouring agents such as solvent red, acid blue 3,
active agents such as fluorides, preferably, in the form of tertiary amines, such as amine fluoride or organic fluoride such as sodium monofluorophosphate, potassium nitrate, and/or oxalate, potassium nitrate.

An oral care foam is a dental care product that can be directly sprayed into the mouth. Then, the mouth is rinsed with the foam, and the foam is spat out. This allows for cleaning the teeth, basically, anywhere, and without need for a toothbrush. Oral care foams may be used as an additional daily oral care, e.g., and after each meal or drink when using toothbrush is difficult or inconvenient. For example, they may be used when travelling or during the day. They are also suitable for those who wear braces or other orthodontic constructions. An oral care foam may, e.g., comprise Water, Sodium Citrate, Zink Lactate, Xylitol, Hydrogenated starch hydrolysate, D-Panthenol USP, Stevia Extract, Glycerol, Alpin Rose Active, Siberian Ginseng Pro, Sodium Lauroyl Sarcosinate, Sodium Hydroxide Solution 1 N, Oligopeptide-104, Citric acid, L-Menthol, Propylene Glycol, mint oil (*Mentha arvensis*), Glycolipids, Sodium Benzoate, Potassium Sorbate, Omyadent 100-OG.

Due to the herb extract or herb extracts contained in the dental care product of the invention, the care dental care product has a senolytic effect when administered to the gums of a subject. Further, the care dental care product has an anti-inflammatory effect when administered to the gums of a subject.

Thus, the invention also provides a pharmaceutical composition comprising the dental care product of the invention. It can be alternatively be classified as a cosmetic or a medicinal product, which depends on national legislation.

Specifically, the invention provides a method of treating gingivitis, periodontitis or peri-implantitis in a subject, comprising administering an effective amount of the dental care product of the invention to the gums of the subject. Periodontal disease and its early stage, gingivitis, are inflammatory conditions affecting the periodontium, i.e., the tissues that surround and support the teeth. Similarly, peri-implantitis is an inflammatory condition of the tissues surrounding a dental implant. The inventors have surprisingly found that these conditions can be successfully treated by the dental care products of the invention. These can be administered to the gums of a subject afflicted with said disease. Alternatively, they can prevent the disease in a subject not yet affected. The invention provides a method for eliminating or reducing the number of senescent cells in the gums of a subject, comprising administering an effective amount of the dental care product of the invention to the gums of the subject. Further, the invention provides a method for stabilizing at least one loose tooth, comprising administering an effective amount of the dental care product of the invention to the gums of the subject. The dental care product of the invention may also be used to improve wound healing, in particular, for wounds of the gums.

Administration to the gums of the subject may take place during the normal use of the dental care product, e.g., tooth brushing with a tooth paste, tooth gel or tooth mousse of the invention, or rinsing with a mouthwash or oral care foam.

Typically, the dental care product of the invention is administered both to the gums and the teeth of the subject.

Thus, the invention also provides a method for tooth whitening, comprising administering an effective amount of the dental care product of the invention to a tooth of a subject, typically, to the teeth of the subject.

The present invention also relates to cosmetic use of the dental care product of the invention for tooth whitening. A method of tooth whitening for cosmetic reasons is also disclosed, comprising administering the dental care product of the invention to a tooth. In the context of the invention, unless explicitly mentioned or clear from the context, "a" is not limited to the singular, but can also mean "one or more". For example, reference to "a tooth" includes the option that more than one tooth, in particular, all teeth of one person, are designated. The dental care product of the invention may also be used for whitening crowns, implants, filling materials and other oral appliances.

In the method of the invention, the composition is preferably administered one, two or three times a day on 1, 2, 3, 4, 5, 6, 7 or more days, in one embodiment, daily. It can also be administered less often, e.g., once a week or once a month. Frequency of administration is strongly dependent on the whitening effect desired by the user, as well as on the amount of mechanical abrasion to which the teeth are subjected. This includes life-long administration, preferably starting after the permanent teeth have erupted, in particular, after discoloration of a tooth has been noticed. Administration means that a gums or tooth, or, preferably, all teeth of a person are contacted with the dental care product in the way this respective type of product is typically used. For example, a toothpaste is typically used to brush teeth for a time of 1-5 minutes, in particular, about 2-3 minutes.

As the dental care product of the invention does not lead to the undesired side effects of bleaching products comprising peroxides, it can be used daily for all cycles of dental care without harm to the teeth or the gums. Additionally, the product can be used to inhibit the demineralisation of teeth. In particular, the dentifrice or toothpaste of the invention may be used for every brushing of teeth.

Alternatively, it may be used in addition to or alternately with a different dentifrice, e.g., an alternative fluoride containing toothpaste. For example, an alternative fluoride containing toothpaste may be used in the mornings, and the toothpaste of the invention may be used in the evening after the last meal of the day. The dental care product may also be used after normal dental care, e.g. in the evening after brushing teeth.

Advantageously, administering an effective amount of the dental care product of the invention to the gums and teeth of a subject simultaneously has the effect of tooth whitening, eliminating or reducing the number of senescent cells in the gums of a subject, and preventing caries. The dental care product of the invention may thus be for use in treatment of any or all of these conditions.

In summary, in contrast to most state of the art methods of tooth whitening, the method of the invention does not irritate the gums of the subject, but instead helps to address issues such as inflammation and aging of the gums that are otherwise often exacerbated by tooth whitening treatment. Thus, in one embodiment, the dental care product of the invention is used by a subject who has used bleaching agents such as peroxide for tooth whitening, and at least one side effect like demineralisation, erosion and tooth sensitivity has been caused by said treatment. In this context, the dental care product of the present invention leads to further tooth whitening while at the same time helping to treat the side effects, treat periodontal disease, to rejuvenate the gums and/or restore the well-being of the subject.

The following examples are intended to illustrate, but not to limit the invention. All literature cited in the present application is herewith incorporated herein in full.

EXAMPLES

Example 1

Materials and Methods

Suspensions of oligopeptide 104 (5 mg/ml) with or without hydroxyapatite particles (average size d50≤300 nm (Horiba); 40-60% crystallinity, 25 wt %) were generated.

The suspensions were directly applied onto an enamel surface of a tooth, and residues washed off (10 sec). The specimen was stored in distilled water for 24 hours at 37° C. The procedure was repeated 3 times.

The tooth colour was measured with a dental spectrophotometer (VITA Easyshade). The illumination conditions were standardized with a black box as the background for the teeth during the measurement. The tip was applied perpendicular to the tooth surface and the average L*a*b-values from three repetitions were used for evaluations. Colour measurement were done at baseline (t1=without treatment), 24 hours after first application (t1), 24 hours after second application (t3), 24 hours after the third application (t4).

The mean changes of the L*a*b-values between different measurements in each group were expressed as ☐E (according to ISO 28399).

Results

The results are provided in Table 1 below:

TABLE 1

|  | Control (HA only) | Test (HA + oligopeptide 104) |
|---|---|---|
| ☐E (t2-t1) - 1$^{st}$ application | 2.3 | 4.6 |
| ☐E (t3-t2) - 2$^{nd}$ application | 1.1 | 1.9 |
| ☐E (t4-t3) - 3$^{rd}$ application | 1.5 | 0.6 |

The experiment shows that, surprisingly, the combination of a protein matrix according to the invention with HA significantly increases the whitening effect seen upon application of HA only.

Of note, the results are provided as ΔE for the different time points as described in the first column of the table. Accordingly, the ΔE values show the additional increase in between the applications. To calculate the total effect of all application, the ΔE values have to be added. The calculation shows that total ΔE for the control (HA only) is 4.9, and total ΔE for the combination (HA+oligopeptide 104) is 7.5. Therefore, there was an improvement with each application as compared to control.

However, the improvement is limited by a kind of saturation of the tooth surface with light scattering particles. While the combination of HA+oligopeptide 104 already attaches nearly the optimum amount of HA particles with one application, the HA only control group needs more than one application to attach as many HA particles as possible to the tooth surface. This explains why ΔE is higher for the HA+oligopeptide group after the first application and why the increase (not the total ΔE) is higher for the HA only control after the third application. The HA only group could thus still benefit more from the additional applications, while the HA+oligopeptide group already was close to the optimum after one application, and thus, consecutive applications still showed some improvement at a high level, but not as much as the first application.

This demonstrates that, while HA alone has a whitening effect, the effect of the combination is surprisingly much higher.

The mean degree of tooth whitening is comparable to state of the art chemical bleaching methods (e.g., leading to ΔE of ΔE of less than 4 for home bleaching, ΔE of about 2.4-5.7 after 7 days, or 2.9-5.5 after 14 days for whitening strips, and up to ΔE 12 for power bleachings (in-office use only) (Gerlach et al., 2002; Demarco et al., 2009; Delfino et al., 2009.)

However, the dental care product and method of the invention has significant advantages over chemical bleaching with regard to undesired effects such as tooth erosion, increased tooth sensitivity etc.

To demonstrate that the effect of the combination of self-assembling peptides and calcium phosphate particles is synergistic, the experiment as described above were repeated with self-assembling peptide alone (without excipients). Oligopeptide 104 was used in a concentration of 7.5 mg/mL, i.e., the concentration was higher than the concentration of peptide used in the application alone. ΔE was determined 24 h after application, with three measurements per tooth and 10 teeth examined. ΔE was 0.62. Accordingly, the self-assembling peptide alone did not have a noticeable whitening effect. With ΔE of 2.3 for HA alone after 24 h, the effect of the combination of self-assembling peptide and HA shown in the application as filed of ΔE 4.6 has to be considered a synergistic effect.

Example 2

The antimicrobial activity and the cytotoxic effect exerted by leaf extracts from plants of the genus *Rhododendron* towards epidermal and intestine epithelial cells was tested by Rezk A, et al. (2005. BMC Complement Altern Med. 2015; 15:364).

It was shown that extracts of *Rhododendron ferrugineum* had potent antimicrobial activity and were not toxic towards IEC6 cells.

The experiment as described therein is repeated with oral mucosal cells and an extract from *Rhododendron ferrugineum* (e.g., available from Mibelle Biochemistry, Mibelle AG (Buchs, Aargau, Switzerland) at concentrations of 1, 2 and 3% (w/w). Antimicrobial activity against bacteria associated with periodontal disease, i.e., are predominantly gram-negative anaerobic bacteria such as *A. actinomycetemcomitans, P. gingivalis, P. intermedia, B. forsythus, C. rectus, E. nodatum, P. micros, S. intermedius* and *Treponema sp.* is tested.

Example 3

For the study of the effect of the plant extracts, a Scratch Test or wound healing assay is used to determine the positive effect on wound healing of the extract.

A wound healing assay is a laboratory technique used to study cell migration and cell-cell interaction. This is also called a scratch assay, because it is done by making a scratch on a cell monolayer and capturing images at regular intervals by time lapse microscope.

It is specifically a 2D cell migration approach to semi-quantitatively measure cell migration of a sheet of cells. This scratch can be made through various approaches, such as mechanical, thermal, or chemical damage. The purpose of this scratch is to produce a cell-free area in hopes of inducing cells to migrate and close the gap. The scratch test is only ideal for cell types that migrate as a collective epithelial sheets and not useful for non-adherent cells. (https://en.wikipedia.org/wiki/Wound healing assay). The scratch test can be carried out, e.g., as described in Rodriguez L G, et al. (2005. Methods in Molecular Biology. 294: 23-9).

The extracts from *Rhododendron ferrugineum* (e.g., available from Mibelle Biochemistry, Mibelle AG (Buchs, Aargau, Switzerland)), *Leontopodium alpinum* Flower/Leaf Extract (e.g., available from Lipoid Kosmetik AG (Steinhausen, Switzerland)) and Siberian ginseng (e.g., available from Lipoid Kosmetik AG (Steinhausen, Switzerland)) are separately and in combination tested in a scratch test, e.g., at a concentration of 2% (w/w) each, using oral mucosal epithelial cells.

EMBODIMENTS OF THE INVENTION

The invention for example provides the following embodiments:
1. A dental care product comprising
a) 0.4-40 wt % calcium phosphate particles having a size of 0.01-50 μm,
b) 0.001-5 wt % of a self-assembling peptide consisting of SEQ ID NO: 1,
c) 0.01-5 wt % of an extract of a plant of the genus *Rhododendron*, and
d) 0.01-5 wt % of an extract of a plant of the genus *Leontopodium*.
2. The dental care product of embodiment 1, wherein the concentration of self-assembling peptide is 0.001-0.5 wt %, optionally, 0.01-0.05 wt %.
3. The dental care product of any of embodiments 1 or 2, wherein said plant of the genus *Rhododendron* is *Rhododendron ferrugineum*.
4. The dental care product of any of embodiments 1 or 2, wherein said plant of the genus *Rhododendron* is *Rhododendron hirsutum*.
5. The dental care product of any of embodiments 1-4, wherein the dental care product comprises 1-2 wt % of an extract of said plant of the genus *Rhododendron*.
6. The dental care product of any of embodiments 1-5, wherein said plant of the genus *Leontododium* is *Leontopodium nivale, Leontopodium albogriseum, Leontopodium andersonii, Leontopodium antennarioides, Leontopodium artemisiifolium, Leontopodium aurantiacum, Leontopodium beerianum, Leontopodium blagoveshczenskyi, Leontopodium brachyactis, Leontopodium calocephalum, Leontopodium campestre, Leontopodium chuii, Leontopodium conglobatum, Leontopodium coreanum, Leontopodium dedekensii, Leontopodium delavayanum, Leontopodium discolor, Leontopodium fangingense, Leontopodium fauriei, Leontopodium forrestianum, Leontopodium franchetii, Leontopodium giraldii, Leontopodium gracile, Leontopodium haastioides, Leontopodium haplophylloides, Leontopodium hayachinense, Leontopodium himalayanum, Leontopodium jacotianum, Leontopodium japonicum, Leontopodium kamtschaticum, Leontopodium kurilense, Leontopodium leiolepis, Leontopodium leontopodinum, Leontopodium longifolium, Leontopodium melanolepis, Leontopodium meredithae, Leontopodium micranthum,*

*Leontopodium microphyllum, Leontopodium monocephalum, Leontopodium muscoides, Leontopodium nanum, Leontopodium niveum, Leontopodium ochroleucum, Leontopodium omeiense, Leontopodium palibinianum, Leontopodium pusillum, Leontopodium roseum, Leontopodium rosmarinoides, Leontopodium shinanense, Leontopodium sinense, Leontopodium smithianum, Leontopodium souliei, Leontopodium stellatum, Leontopodium stoechas, Leontopodium stoloniferum, Leontopodium stracheyi, Leontopodium subulatum, Leontopodium villosulum, Leontopodium villosum, Leontopodium wilsonii.*

7. The dental care product of any of embodiments 5 or 6, wherein said plant of the genus *Leontododium* is *Leontopodium nivale*.

8. The dental care product of any of embodiments 1-7, further comprising e) an extract of a plant of the genus *Eleutherococcus*, optionally, *Eleutherococcus senticosus*.

9. The dental care product of any of embodiments 1-8, wherein said extract of c) is a glycerinic extract.

10. The dental care product of any of embodiments 1-9, comprising an extract of d), wherein said extract of d) is a glycerinic extract.

11. The dental care product of any of embodiments 1-10, comprising an extract of e), wherein said extract of e) is a glycerinic extract.

12. The dental care product of any of embodiments 1-8, wherein said extract of c), is an alcoholic extract, e.g., an ethanolic extract.

13. The dental care product of any of embodiments 1-8 and 12, comprising an extract of d), wherein said extract of d) is an alcoholic extract, e.g., an ethanolic extract.

14. The dental care product of any of embodiments 1-8 and 12-13, comprising an extract of e), wherein said extract of e) is an alcoholic extract, e.g., an ethanolic extract.

15. The dental care product of any of embodiments 1-14, wherein said extract of c) is an extract of the leaves and/or flowers of the plant, optionally, of the leaves and flowers of the plant.

16. The dental care product of embodiment 15, wherein said extract of c) is an extract of the leaves of the plant.

17. The dental care product of any of embodiments 15-16, wherein said extract of c) is an extract of the flowers of the plant.

18. The dental care product of any of embodiments 1-17, comprising 0.5-3 wt % of said extract of c), optionally, 1-2 wt %.

19. The dental care product of any of embodiments 1-18, comprising an extract of d), wherein said extract of d) is an extract of the leaves and/or flowers of the plant, optionally, of the leaves and flowers of the plant.

20. The dental care product of embodiment 19, wherein said extract of d) is an extract of the leaves of the plant.

21. The dental care product of any of embodiments 19-20, wherein said extract of d) is an extract of the flowers of the plant.

22. The dental care product of any of embodiments 1-21, comprising 0.5-3 wt % of said extract of d), optionally, 1-2 wt %.

23. The dental care product of any of embodiments 1-22, comprising e) an extract of e), wherein said extract of e) is an extract of the roots, berries and/or leaves of the plant, optionally, of the whole of the plant.

24. The dental care product of embodiment 23, wherein said extract is an extract of the roots of the plant.

25. The dental care product of any of embodiments 23-24, comprising 0.5-3 wt % of said extract of e), optionally, 1-2 wt %.

26. The dental care product of any of embodiments 1-25, wherein the self-assembling peptide is in assembled form.

27. The dental care product of any of embodiments 1-26, wherein said calcium phosphate particles comprise hydroxyapatite, and, optionally, consist thereof.

28. The dental care product of any of embodiments 1-27, wherein 30-70% of said calcium phosphate particles have a size of 200-600 nm.

29. The dental care product of any of embodiments 1-28, wherein the dental care product is selected from the group consisting of toothpaste, tooth gel, mouthwash, mouth spray and oral care foam.

30. The dental care product of any of embodiments 1-29, wherein the dental care product is toothpaste.

31. The dental care product of any of embodiments 1-29, wherein the dental care product is mouthwash.

32. The dental care product of any of embodiments 1-29, wherein the dental care product is mouth spray.

33. The dental care product of any of embodiments 1-29, wherein the dental care product is oral care foam.

34. The dental care product of any of embodiments 1-33, comprising 0.5-40 wt % of said calcium phosphate particles and 0.001-1 wt %, optionally, 0.05 wt %, of said self-assembling peptide, wherein the dental care product is a toothpaste.

35. The dental care product of any of embodiments 1-34, wherein the care dental care product has a senolytic effect when administered to the gums of a subject.

36. The dental care product of any of embodiments 1-35, wherein the care dental care product has an anti-inflammatory effect when administered to the gums of a subject.

37. A pharmaceutical composition comprising the dental care product of any of embodiments 1-36.

38. A method of treating periodontal disease or peri-implantitis in a subject, comprising administering an effective amount of the dental care product of any of embodiments 1-37 to the gums of the subject.

39. The method of embodiment 38, wherein the periodontal disease is gingivitis.

40. The method of embodiments 38, wherein the periodontal disease is periodontitis.

41. The method of embodiment 38, wherein the method is a method of treating peri-implantitis.

42. A method for eliminating or reducing the number of senescent cells in the gums of a subject, comprising administering an effective amount of the dental care product of any of embodiments 1-37 to the gums of the subject.

43. A method for stabilizing at least one loose tooth, comprising administering an effective amount of the dental care product of any of embodiments 1-37 to the gums of the subject.

44. A method for tooth whitening, comprising administering an effective amount of the dental care product of any of embodiments 1-37 to a tooth of a subject, wherein the composition is optionally administered one, two or three times a day on 1, 2, 3, 4, 5, 6, 7 or more days, e.g., daily.

45. The method of embodiment 44, wherein the method is a cosmetic method.

46. The method of any of embodiments 38-45, which is a method of tooth whitening, eliminating or reducing the number of senescent cells in the gums of a subject, and treating periodontal disease, comprising administering an effective amount of the dental care product of any of embodiments 1-37 to the gums and teeth of a subject.

LITERATURE

Dabanoglu et al., 2009, Am J Dent 22:23-29.
Dahl et al., 2003, Crit Rev Oral Biol Med 14(4):292-304.

Delfino et al., 2009, J Appl. Oral Sci 17(4):284-8.
Demarco et al., 2009. Braz Oral Res. 23 Suppl 1:64-70.
Gerlach et al., 2002. Am J Dent. 15 Spec No:7A-12A.
Jiang et al, 2008, J Dent 36(11): 907-914.
Jin et al., 2013, Eur I Oral Sci 121: 382-388.
Lim et al., 2009, Biomed Mater 4(2): 025017.
Mohd et al., 2007, Biomed Mater Eng 17(2): 69-75.
Nagelberg, R. H., 2014. https://www.dentaleconomics.com/practice/article/16390423/tooth-whitening
Niwa et al. J Mater Sci Mater Med 2001; 12: 277-281.
Raoufi, S. and D. Birkhed (2010). Int Dent J60(6): 419-423.
Rezk A, et al. (2005. BMC Complement Altern Med. 2015; 15:364
Rodriguez L G, et al. (2005. Methods in Molecular Biology. 294: 23-9
Roveri, Battistelli et al., 2009, J Nanomaterial, special issue, Article ID 746383
EP 1 762 215 A1, EP 2 327 428 A2
US 20050037948 A1, US 20080075675 A1, US 2008199431 A1, US 20100247589 A1, US 20100297203 A1, US 2010/0247457 A1
U.S. Pat. No. 6,548,630
WO 2004/007532 A1, WO 2006/073889 A2, WO 2007/000979 A1, WO 2006/047315 A2, WO 2007/137606 A1, WO 2008/113030 A2, WO 2009/026729 A1, WO 2010/041636 A1, WO 2010/103887 A1, WO 2013/068020 A1, WO2010/019651 A1, WO 2015/044268 A1, WO 2018/033570 A1
JP2008/081424, JPH115722
JPH115722, JP2008/081424, JP 2007/0176862, JP 2001/131041, CN101385856

---

---

What is claimed is:

1. Dental care product comprising
   a) 0.4-40 wt % calcium phosphate particles having a size of 0.01-50 μm,
   b) 0.001-5 wt % of a self-assembling peptide consisting of SEQ ID NO: 1,
   c) 0.1-5 wt % of an extract of a plant of the genus *Rhododendron*, and
   d) 0.1-5 wt % of an extract of a plant of the genus *Leontopodium*.

2. The dental care product of claim 1, wherein said plant of the genus *Rhododendron* is *Rhododendron ferrugineum* or *Rhododendron hirsutum*.

3. The dental care product of claim 2, wherein the dental care product comprises 1-2 wt % of an extract of *Rhododendron ferrugineum*.

4. The dental care product of claim 3, wherein said plant of the genus *Leontododium* is *Leontopodium nivale*.

5. The dental care product of claim 1, wherein said extract of c) and/or d), optionally, of c) and d), is a glycerinic extract.

6. The dental care product of claim 1, wherein said extract is an extract of the leaves and/or flowers of the plant of c) and/or d), optionally, of c) and d).

7. The dental care product of claim 1, wherein said extract is an extract of the flowers of the plant of c) and/or d), optionally, of c) and d).

8. The dental care product of claim 1, further comprising e) an extract of a plant of the genus *Eleutherococcus*, optionally, *Eleutherococcus senticosus*.

9. The dental care product of claim 1, wherein the self-assembling peptide is in assembled form.

10. The dental care product of claim 1, wherein said calcium phosphate particles comprise hydroxyapatite.

11. The dental care product of claim 1, wherein 30-70% of said calcium phosphate particles have a size of 200-600 nm.

12. The dental care product of claim 1, wherein the dental care product is selected from the group consisting of toothpaste, tooth gel, mouthwash, mouth spray and oral care foam.

13. The dental care product of claim 1, comprising 0.5-40 wt % of said calcium phosphate particles and 0.02-1 wt % of said self-assembling peptide, wherein the dental care product is a toothpaste.

14. The dental care product of claim 1, wherein the care dental care product has a senolytic effect when administered to the gums of a subject.

15. The dental care product of claim 1, wherein the care dental care product has an anti-inflammatory effect when administered to the gums of a subject.

16. A pharmaceutical composition comprising the dental care product of claim 1.

17. A method of treating periodontal disease or peri-implantitis in a subject, comprising administering an effective amount of the dental care product of claim 1 to the gums of the subject.

18. A method for eliminating or reducing the number of senescent cells in the gums of a subject, comprising administering an effective amount of the dental care product of claim 1 to the gums of the subject.

19. A method for tooth whitening, comprising administering an effective amount of the dental care product of claim 1 to a tooth of a subject.

20. The method of claim 17, which further is a method of tooth whitening, and of eliminating or reducing the number of senescent cells in the gums of a subject, comprising administering an effective amount of the dental care product of claim 1 to the gums and teeth of a subject.

21. The dental care product of claim 1, comprising 0.05 wt % of said self-assembling peptide, wherein the dental care product is a toothpaste.

22. The method of claim 19, wherein the composition is administered one, two or three times a day on 1, 2, 3, 4, 5, 6, 7 or more days.

23. The method of claim 19, wherein the composition is administered daily.

* * * * *